Figure 1:
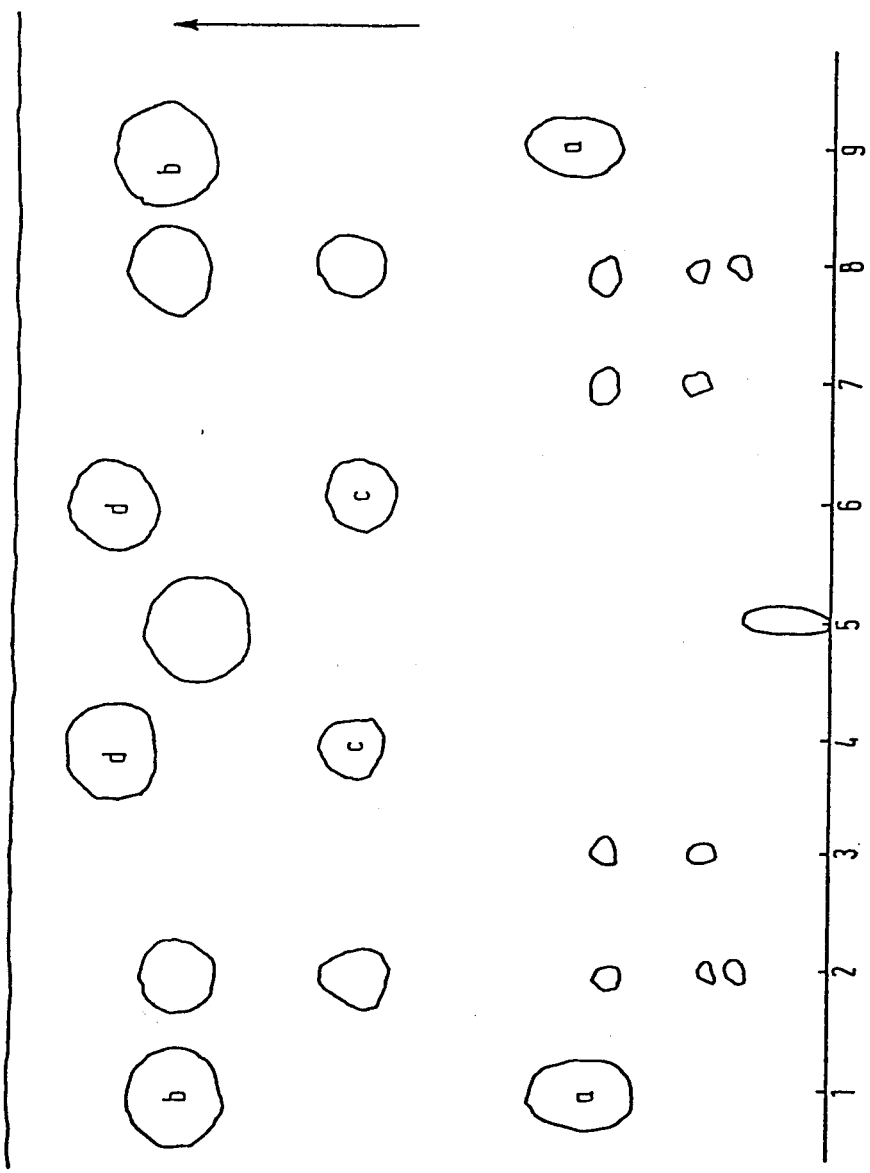

United States Patent [19]

Boettcher et al.

[11] 4,287,190

[45] Sep. 1, 1981

[54] COMPLEXES OF BIVALENT COPPER

[76] Inventors: Barry Boettcher, 12 Mahogany Dr., New Lambton, N.S.W.; William R. Walker, 36 Stanley St., Merewether, N.S.W.; Michael W. Whitehouse, Dept. of Experimental Pathology, Australian National University, Canberra, A.C.T., all of Australia

[21] Appl. No.: 98,344

[22] Filed: Nov. 29, 1979

Related U.S. Application Data

[63] Continuation-in-part of Ser. No. 963,755, Nov. 27, 1978, abandoned.

[30] Foreign Application Priority Data

Aug. 15, 1979 [AU] Australia .............................. PE0041

[51] Int. Cl.³ ............................................. A61K 31/60
[52] U.S. Cl. .................................. 424/230; 260/438.1
[58] Field of Search ...................... 260/438.1; 424/230

[56] References Cited

U.S. PATENT DOCUMENTS

| 3,884,949 | 5/1975 | Eicke et al. | 260/438.1 X |
| 4,020,180 | 4/1977 | Woerner | 260/438.1 X |

OTHER PUBLICATIONS

Chemical Abstracts 73 115882p (1970).
Chemical Abstracts 69 113013z (1968).
Chemical Abstracts 84 38591r (1976).
Chemical Abstracts 84 159683f (1976).
Chemical Abstracts 85 116777t (1976).

*Primary Examiner*—Helen M. S. Sneed
*Attorney, Agent, or Firm*—Ostrolenk, Faber, Gerb & Soffen

[57] ABSTRACT

Compositions containing neutral copper complexes, particularly copper-salicylate complexes having the formula $Cu[C_6H_4(X)COO]_2 \cdot Y$ in which Y represents dimethylsulfoxide, dimethylformamide or an alkanol and in which X is preferably —OH, together with a pharmaceutically acceptable, non-aqueous carrier have been found to have therapeutic activity in the treatment of inflammatory diseases. The compositions have been found particularly suitable for the treatment of arthritis.

19 Claims, 2 Drawing Figures

COMPLEXES OF BIVALENT COPPER

This is a continuation-in-part of application Ser. No. 963,755, filed Nov. 27, 1978, and now abandoned.

FIELD OF THE INVENTION

This invention relates to novel anti-inflammatory compositions containing copper complexes and processes utilizing such compositions.

DESCRIPTION OF PRIOR ART

Many studies of the role of copper, and especially complexes of copper, in the treatment of inflammatory diseases have been reported in recent years. One of the most recent studies describes the use of parenterally administered copper complexes, and particularly copper (II) salicylate, in the treatment of rheumatic disease (Sorenson and Hangarter, Inflammation, 2, 217–238 (1977)).

The prior art describes a wide variety of copper-salicylate complexes prepared by the reaction of inorganic copper (II) salts with salicylic acid in aqueous solution. The specific complex formed in aqueous solution has been found to depend on the pH of the aqueous solution and both neutral complexes such as the pale blue crystalline bis (salicylato) copper (II) tetrahydrate

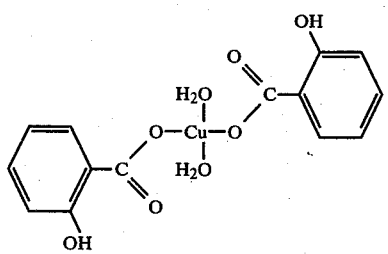

and anionic complexes such as the olive green sodium salicylatocuprate (II)

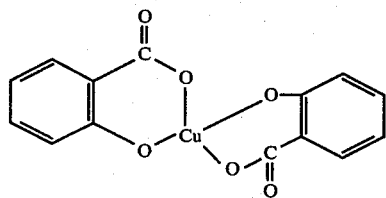

are known in the art.

Kratsmar - Smogrovic et al, Chemical Abstracts, 69, 25 (1968) and Chem. Zvesti, 22, No. 7 (1968) describe the preparation of compound indicated as $Cu[H\ Sal]_2 \cdot C_2H_5OH$ by dissolving bis (salicylato-) - diaquo - copper (II) -dihydrate and salicylic acid in 96% ethanol, i.e. in a water-containing environment. However, the presence of water would in fact have resulted in the formation of polymers of general formula $[Cu\ (Sal)]n \cdot x\ H_2O$ and complexes of $[Cu(Sal)]_n \cdot x\ H_2O \cdot y\ C_2H_5OH$.

This is confirmed by the observations of Suntsov et al Dokl. Akad. Nauk. S.S.R. 179, 1352 (1968) who showed that when copper salicylate tetrahydrate was dissolved in alcohol together with a small quantity of salicylic acid and a little water, the product was $Cu[H\ Sal]_2 \cdot C_2H_5OH \cdot H_2O$.

Neither Kratsmar - Smogrovic et al nor Suntsov et al were concerned with possible therapeutic properties of the products which they prepared, and in fact, such products would have no therapeutic value as they break down in water and polymerise in ethanol.

SUMMARY OF PRESENT INVENTION

It is an object of this invention to provide novel therapeutic anti-inflammatory compositions comprising neutral copper complexes prepared by the reaction of copper compounds and substituted benzoic acids in non-aqueous solvents, and a pharmaceutically acceptable carrier. A further object of the invention is to provide a method for the treatment of inflammatory diseases of animals by the administration of said compositions. A still further object of the invention is to provide a method for the preparation of the said compositions.

Accordingly, in one embodiment the invention provides therapeutic compositions comprising one or more neutral copper complexes of the formula $Cu[C_6H_4\ (X)\ COO]_2 \cdot Y$ wherein Y represents dimethylsulfoxide, dimethylformamide or an alkanol, preferably a $C_1$ to $C_6$ aliphatic alkanol, and wherein X can be located in any position and is OH, SH, SeH, $NH_2$ or

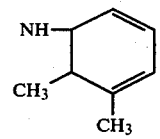

and a pharmaceutically acceptable carrier comprising excess salicylic acid or the relevant substituted salicylic acid, an excess of the dimethylsulfoxide, dimethylformamide or alkanol as the case may be, and an emollient, for example glycerol.

Optimally the composition may also contain a buffer for increasing the pH to prevent irritation by the salicylic acid; such buffers may include, for example, sodium acetate.

Although in no way wishing to be bound by theory, as a result of physico-chemical studies, the complexes of the invention are of the following dimeric structure:

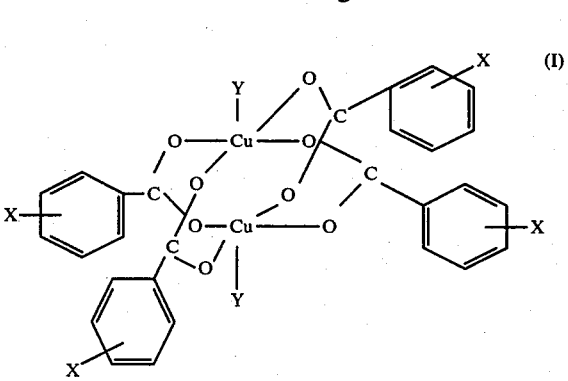

The preferred compound according to the invention is the copper salicylate complex which is of the formula:

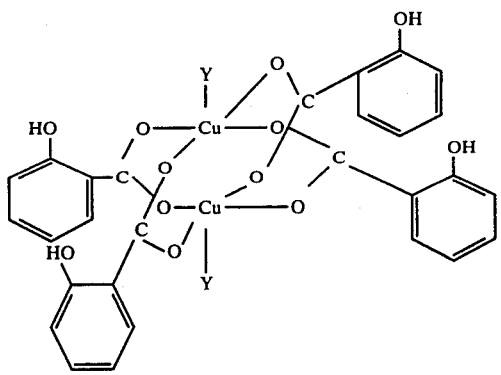

(II)

and particularly the compound in which Y is dimethylsulfoxide.

The compounds of the invention may be prepared by reacting inorganic copper (II) compounds, for example copper salts or cupric hydroxide, with the appropriate substituted benzoic acid in the presence of the chosen solvent, viz dimethylsulfoxide, dimethylformamide or alkanol.

For example, reaction of cupric hydroxide with salicylic acid in anhydrous ethanol gives the complex of formula $Cu[C_6H_4(OH)COO]_2$. $C_2H_5OH$, hereinafter referred to by the formula $Cu[H\ Sal]_2$. $C_2H_5OH$, which forms deep green crystals when crystallised from anhydrous ethanol containing excess (approx. 5 M) salicylic acid.

Again by reacting cupric hydroxide with salicylic acid and dimethylsulfoxide, fine deep green needles of $Cu[H\ Sal]_2$ DMSO can be obtained.

The compounds of the invention have been found to be particularly useful in the treatment of inflammatory diseases in animals. Thus in a further embodiment, the invention provides a process for the treatment of inflammatory diseases of animals which process comprises administering to said animals an effective amount of a composition of the invention as hereinbefore defined.

The compounds of the invention have proved particularly effective in alleviating the symptoms of inflammatory diseases such as rheumatic disease, arthritis and rheumatoid arthritis when applied topically to the animal.

The compositions are particularly suitable for topical application to animals to be treated and therefore may be in the form of a gel, an ointment, a paste, a cream or a lotion. Compositions comprising a compound of the invention in solution are preferred as they are more efficient in perfusing the skin.

The therapeutically active components of the compositions of the invention are unstable in the presence of water and therefore the compositions are prepared in a non-aqueous environment. In addition to the carrier materials referred to above, the compositions of the invention may include a further non-aqueous lipophilic carrier; suitable carriers include monohydric, dihydric and trihydric alkanols such as, for example: short chain ($C_1$ to $C_{10}$) and long chain $C_{12}$ to $C_{20}$ alcohols including methanol, ethanol, propanol, butanol and cetyl alcohol; dihydric alcohols such as diethylene glycol; and polyhydric alcohols such as glycerol.

The amount of the compound of the invention employed in the compositions will depend to a large extent on the inflammatory condition being treated. However, as a general rule, the compositions may comprise from 0.1 to 15% w/v of the copper compounds of the invention and preferably from 1 to 7% w/v.

As previously indicated, the compounds of the invention have proved particularly useful in the alleviation of the symptons of inflammatory disease when applied topically to the animal in the form of a pharmaceutical composition as hereinbefore defined. The compounds are believed to be efficacious in such treatments because of their ready penetration of the skin. Furthermore, the compounds are believed to offer particular advantages in the treatment of inflammatory diseases of humans because of the non-toxic nature of the compounds and evidence that the compounds are readily cleared from the treated animal as indicated by the limited duration of the anti-inflammatory effect of the compounds.

The compositions may comprise, in addition to one or more compounds of the invention, other pharmaceutically active ingredients including other anti-inflammatory agents and conventional pharmaceutical excipients known in the art.

The invention is now illustrated by but not limited to the following examples.

EXAMPLE 1

Preparation of $Cu[H\ Sal]_2$. $C_2H_5OH$.

Freshly prepared $Cu(OH)_2$ (0.97 g) was added to a solution of salicylic acid (6.9 g) in anhydrous ethanol (50 ml). The suspension was then refluxed on a water bath until all the copper hydroxide had reacted. The resultant deep-green-coloured solution was then filtered and green crystals were deposited on cooling. These were filtered off, washed with cold alcohol and air dried. Yield 3.2 g (Found: Cu, 16.6; C, 50.2; H, 4.2; Cu $C_{16}H_{16}O_7$ requires Cu, 16.6; C, 50.1: H, 4.2%).

EXAMPLE 2

Preparation of $Cu[H\ Sal]_2$. $CH_3OH$ and $Cu[H\ Sal]_2.C_3H_7OH$.

$Cu[H\ Sal]_2$. $CH_3OH$, analysed as Cu $C_{15}H_{14}O_7$, and $Cu[H\ Sal]_2$. $C_3H_7OH$, analysed as Cu $C_{17}H_{18}O_7$, were prepared following the procedure described in Example 1 and substituting for anhydrous ethanol, anhydrous methanol and anhydrous n-propanol, respectively.

EXAMPLE 3

This example demonstrates the preparation of a composition comprising $Cu[H\ Sal]_2$. $C_2H_5OH$.

Freshly prepared cupric hydroxide (1.0 g) was added to a solution of salicylic acid (7 g) in anhydrous ethanol (80 ml). The suspension was heated under reflux until all the cupric hydroxide had reacted. The resultant deep-green-coloured solution was filtered to remove any insoluble polymeric copper salicylate and glycerol (20 ml) was added to the filtrate.

The deep-green c. 0.1 M $Cu[H\ Sal]_2$. $C_2H_5OH$ solution obtained by this procedure was found to be stable for a prolonged indefinite period and was used in the tests described in examples 4 and 5.

EXAMPLE 4

This example demonstrates the percutaneous absorption of the compound $Cu[H\ Sal]_2$. $C_2H_5OH$.

Male Wistar rats (average weight 250 g) were anaesthetised with diethyl ether and an area of c 20 sq. cm. was shaven high on their backs. The $Cu[H\ Sal]_2$. $C_2H_5OH$ composition prepared according to example 3 was then applied to each rat (c. 20 ml per 3 rats). The rats were then returned to their cages and after two days their urine was collected and compared with the urine of control, untreated, rats following the procedure below.

Urine (5 ml) was acidified with 2 M $H_2SO_4$ and shaken with ethyl acetate (2 ml). After centrifuging, the ethyl acetate layer was analysed by thin layer chromatography on silica gel (solvent: benzene, diethyl ether, glacial acetic acid and methanol in a ratio of 120:60:18:1 by volume) along with samples of salicylic acid, salicyluric acid, gentisic acid and ethyl salicylate.

The results are shown in FIG. 1 which is a diagrammatic representation of a chromatogram run under the conditions described above with solvent flow from origin line, represented by the points of application of the samples 1 to 9, in the direction of the arrow shown and wherein:

1 and 9 represent the points of application of a sample of a mixture of salicyluric acid (a) and salicyclic acid (b) chromatographed for comparative purposes;

2 and 8 represent the points of application of a sample of the urine extract of rats treated with the Cu[H Sal]$_2$. $C_2H_5OH$ composition;

3 and 7 represent the points of application of a sample of the urine extract of control, untreated, rats;

4 and 6 represent the points of application of a sample of a mixture of gentisic acid (c) and ethyl salicylate (b) chromatographed for comparative purposes; and 5 represents the point of application of a sample of the Cu[H Sal]$_2$. $C_2H_5OH$ composition used to treat the rats.

The chromatograph clearly shows the presence of salicylic acid and gentisic acid in the urine of the Cu[H Sal]$_2$. $C_2H_5OH$ treated rats indicating that the composition has perfused the skin of the rats.

EXAMPLE 5

This example demonstrates the effectiveness of topical application of the compound Cu[H Sal]$_2$. $C_2H_5OH$ in alleviating the symptoms of artificially induced inflammation in rats.

Male Wistar rats (average weight 250 g) were anaesthetised with diethyl ether and an area of c. 20 sq.cm was shaven high on their backs. The rats were then separated into 7 groups. Group 1, the control rats were not treated. Group 2 rats were treated by the application of a mixture of alcohol and glycerol (4:1), the carrier used for the compound Cu[H Sal]$_2$. $C_2H_5OH$. Group 3 rats were treated with a 7% w/v solution of salicylic acid in a mixture of alcohol and glycerol (4:1). Group 4, 5, 6 and 7 rats were treated with amounts of Cu[H Sal]$_2$. $C_2H_5OH$ composition prepared according to example 3 containing 154 mg, 231 mg, 462 mg, and 770 mg respectively, of Cu[H Sal]$_2$. $C_2H_5OH$.

About 6 hours after the topical treatment of the rats, inflammation was induced in a foot of each rat in each of the groups by the injection of 0.1 ml of 1% saline solution of sodium carrageenan into a foot pad of each rat. The inflammation of the feet of the rats in each group was then monitored by the swelling of the feet with a micrometer screw-gauge.

Figure 2:
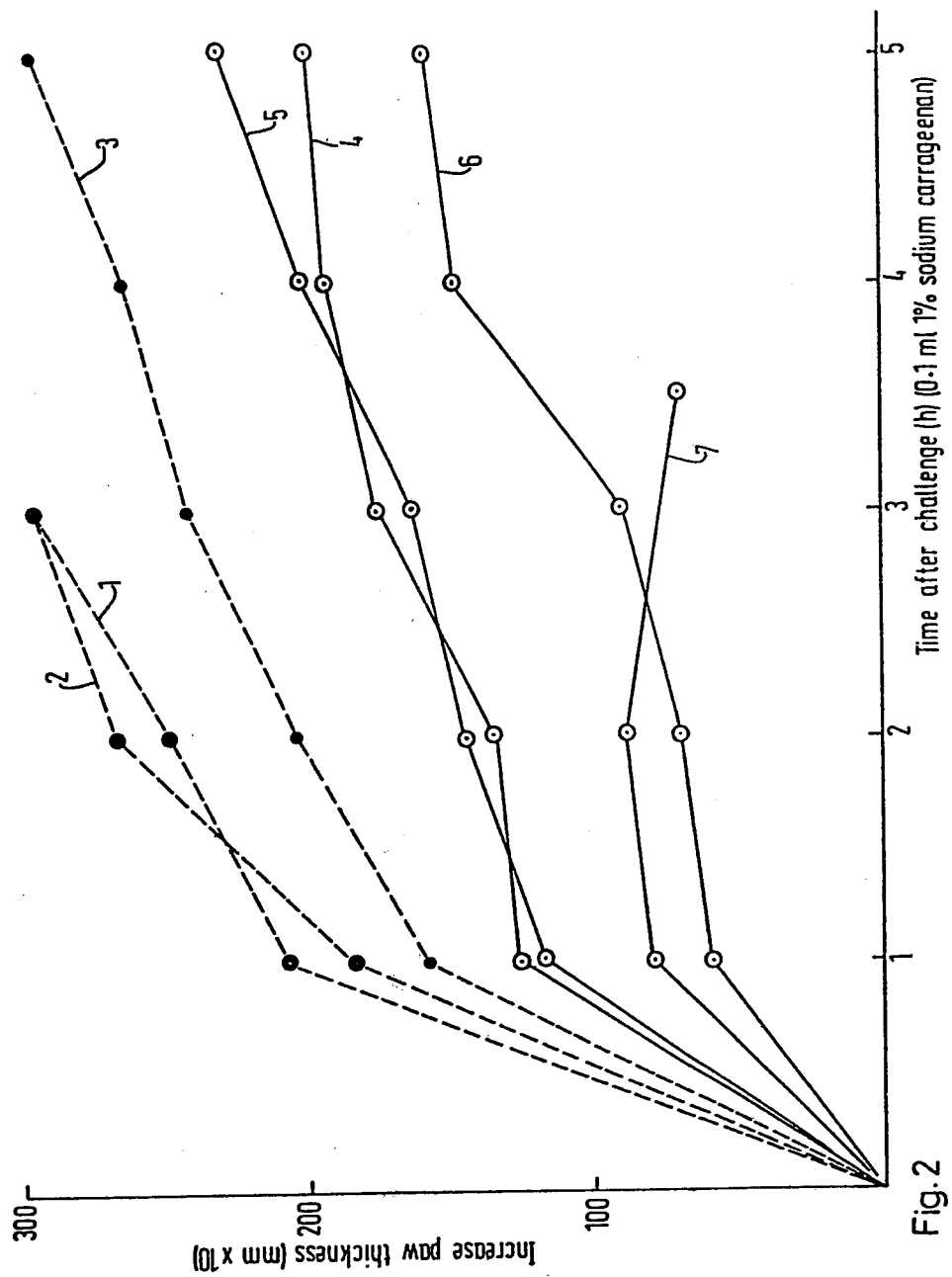

The results are shown in FIG. 2 wherein the curves represent the increase in paw thickness of the rats with time after the injection of the inflammatory agent. The curves 1 to 7 represent the swelling of the paws of the rats of groups 1 to 7 respectively.

FIG. 2 clearly shows the anti-inflammatory effect of the topically applied compound Cu[H Sal]$_2$. $C_2H_5OH$.

EXAMPLE 6

Preparation of Cu[C$_6$H$_4$(SH)COO]$_2$. $C_2H_5OH$.

This compound was prepared as described in Example 1, but substituting 2-thiobenzoic acid (7.7 g) for the salicylic acid. Yield 2.9 g. (Found: Cu 15.6; C 45.9; H 3.6. CuC$_{16}$H$_{16}$O$_5$S$_2$ requires Cu 15.4; C 46.2; H 3.9%).

EXAMPLE 7

Preparation of Cu[C$_6$H$_4$(SeH)COO]$_2$. $C_2H_5OH$.

This compound was prepared as described in Example 1, but substituting 2-selenobenzoic acid (10.0 g) for the salicylic acid. Yield 8.1 g. (Found: Cu 12.3; C 38.1; H 3.5. CuC$_{16}$H$_{16}$O$_5$Se$_2$ requires Cu 12.6; C 37.7; H 3.1%).

EXAMPLE 8

Preparation of Cu[C$_6$H$_4$(NH$_2$)COO]$_2$. $C_2H_5OH$.

This compound was prepared as described in Example 1, but substituting 2-aminobenzoic acid (6.9 g) for the salicylic acid. Yield 5.6 g. (Found: Cu 16.4; C 50.6; H 5.0. CuC$_{16}$H$_{18}$O$_5$N$_2$ requires Cu 16.8; C 50.3; H 4.7%).

EXAMPLE 9

Preparation of Cu[C$_6$H$_4$(OH)COO]$_2$. (CH$_3$)$_2$SO

Cupric hydroxide (1.0 g) and salicylic acid (5.0 g) were dissolved in dimethylsulfoxide (10 ml) and heated on a hot water bath. The solution was refrigerated for 48 hours. Fine deep-green needles were deposited, filtered off, washed with benzene and dried over P$_2$O$_5$ under vacuum. Yield 0.5 g. (Found: Cu 15.5; C 45.9; H 4.0; S 7.8.

CuC$_{16}$H$_{16}$O$_7$S requires Cu 15.4; C 46.1; H 4.3; S 7.8%).

EXAMPLE 10

Preparation of Cu[C$_6$H$_4$. CO$_2$.NH.C$_8$H$_9$]$_2$.$C_2H_5OH$.

This compound was prepared as described in Example 1, but substituting 2-[2,3-dimethylphenyl]aminobenzoic acid (6.8 g) for the salicylic acid. Yield 5.5 g.

(Found: Cu 11.2; C 64.9; H 5.5.% CuC$_{32}$H$_{34}$O$_5$N$_2$ requires Cu 10.9; C 65.1; H 5.8%).

EXAMPLE 11

Preparation of Cu[C$_6$H$_4$(OH)COO]$_2$. C$_3$H$_7$NO

Cupric hydroxide (1.0 g) and salicylic acid (5.0 g) were dissolved in N,N-dimethylformamide (12 ml) and heated on a hot water bath. After refrigerating the resultant solution for 24 hours, green crystals were deposited. These were filtered off, washed with benzene and dried over P$_2$O$_5$ under vacuum. Yield 0.43 g.

(Found: Cu 15.4; C 49.6; H 4.1 and N 3.3% CuC$_{17}$H$_{17}$O$_7$N requires Cu 15.5; C 49.7; H 4.2; N 3.4%.

The anti-inflammatory properties of copper salicylate ethanolate and copper salicylate DMSO formulations are illustrated in the following table.

TABLE

Effect of topically applied copper-salicylates on two rat-paw oedemas in Wistar (W) and Dark Agouti × Lewis (DA × Lew) hybrid rats. All materials applied to shaved dorsal skin in vehicle (= DMSO—glycerol), 4:1 v/v, 5 ml/kg except as noted.

| | % Inhibition of paw oedema induced with: | | | | | | | |
|---|---|---|---|---|---|---|---|---|
| | Carrageenan | | | | Zymosan | | | |
| | W | | DA × Lewis | | W+ | | DA × Lewis | |
| Formulation | 2 Hour | 4 Hour | 2 Hour | 4 Hour | 1 Hour | 2 Hour | 2 Hour | 4 Hour |
| Cu[H Sal]$_2$ . DMSO | 46 | 53 | 47 | 39 | 43 | 21 | 36 | 22 |
| Salicylic acid (alone) | 14 | 18 | 44 | 32 | 22 | 16 | −08 | −05 |
| Vehicle | 15 | 14 | 08 | 06 | 12 | 17 | −06 | −08 |
| Cu(OAc) | 04 | 11 | N/D | | 12 | 12 | 14 | 04 |
| Cu[H Sal]$_2$ . C$_2$H$_5$OH* | | | | | | | | |
| 5 ml/kg | 24 | 32 | | | | | | |
| 15 ml/kg | 58 | 53 | | | | | | |

*Vehicle = ethanol-glycerol (4:1 v/v)
+Because the Wistar rats gave an early peak response to zymosan oedema, only 1 and 2 hour readings are reported.

The Cu[H Sal]$_2$. DMSO formulation has been demonstrated also to be effective on the progress of polyarthritis induced in rats with *Mycobacterium tuberculosis* in squalane.

We claim:

1. A topical anti-inflammatory therapeutic composition comprising an anti-inflammatory effective amount of a neutral copper complex of the formula Cu[C$_6$H$_4$(X)COO]$_2$Y wherein Y represents dimethylsulfoxide, dimethylformamide or an alkanol, and wherein X can be located in any position and is OH, SH, SeH, NH$_2$ or

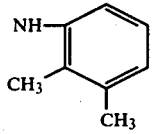

and a pharmaceutically acceptable non-aqueous carrier.

2. A composition according to claim 1, where said pharmaceutically acceptable non-aqueous carrier comprises an emollient and a molar excess with respect to said neutral copper complex of at least one compound selected from the group consisting of salicylic acid, C$_6$H$_4$(X)COOH and Y.

3. A composition according to claim 2, wherein the emollient is glycerol.

4. A composition according to claim 2 wherein the composition also contains a buffer.

5. A composition according to claim 4 wherein the buffer is sodium acetate.

6. A composition according to claim 2 wherein Y is a C$_1$ to C$_6$ aliphatic alkanol.

7. A composition according to claim 2 wherein the complex has the formula

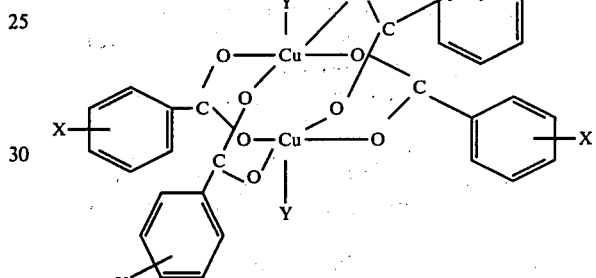

8. A composition according to claim 7 wherein X is OH.

9. A composition according to claim 7 having the formula

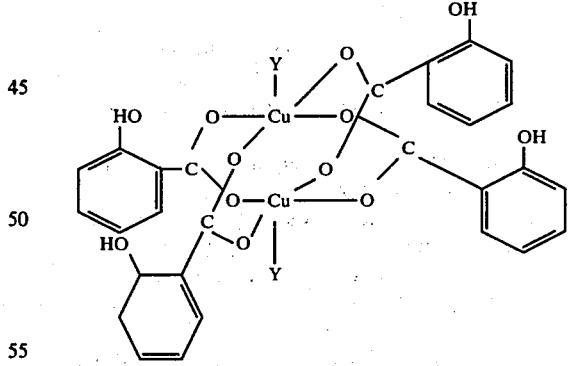

10. A non-aqueous neutral copper complex of the formula Cu[C$_6$H$_4$(X)COO]$_2$ Y wherein Y represents dimethylsulfoxide, and wherein X can be located in any position and is OH, SH, SeH, NH$_2$ or

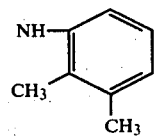

11. The complex of claim 10, having the formula

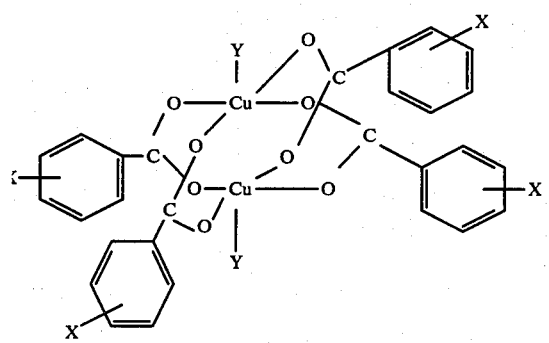

12. The complex of claim 11 wherein X is OH.

13. The complex of claim 12 of the formula

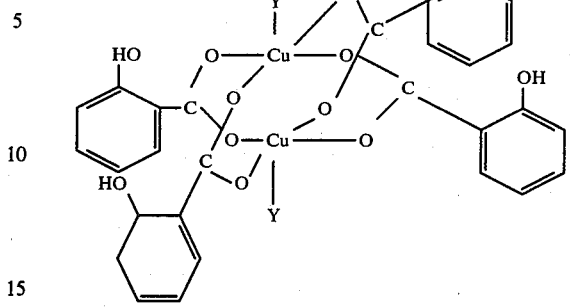

14. A method of preparing the complex according to claim 10, comprising reacting copper (II) hydroxide with a substituted benzoic acid in the presence of dimethyl sulfoxide, or an alkanol under anhydrous conditions.

15. A method according to claim 14 wherein the substituted benzoic acid is salicylic acid.

16. A method according to claim 14 wherein the alkanol is a $C_1$ to $C_6$ aliphatic alkanol.

17. A composition according to claim 1 containing 0.1 to 15% w/v of said copper complex.

18. A method of treating inflammatory diseases comprising topically administering to a patient an anti-inflammatory effective amount of a composition according to claim 1.

19. The copper complex of claim 13 where Y is dimethylsulfoxide.

* * * * *